United States Patent [19]

James

[11] Patent Number: 4,782,181

[45] Date of Patent: Nov. 1, 1988

[54] PROCESS FOR REMOVAL OF HIGH MOLECULAR WEIGHT IMPURITIES IN THE MANUFACTURE OF PURIFIED TEREPHTHALIC ACID

[75] Inventor: David E. James, Batavia, Ill.

[73] Assignee: Amoco Corporation, Chicago, Ill.

[21] Appl. No.: 58,142

[22] Filed: Jun. 4, 1987

[51] Int. Cl.$^4$ ............................................. C07C 51/42
[52] U.S. Cl. ................................. 562/487; 562/412; 562/414; 562/485; 562/486
[58] Field of Search ............... 562/412, 485, 486, 487, 562/414

[56] References Cited

U.S. PATENT DOCUMENTS

| | | | |
|---|---|---|---|
| 3,584,039 | 6/1971 | Meyer | 562/486 |
| 3,726,915 | 4/1973 | Pohlmann | 562/487 |
| 4,405,809 | 9/1983 | Stech et al. | 562/487 |
| 4,626,598 | 12/1986 | Packer et al. | 562/487 |

*Primary Examiner*—Werren B. Lone
*Assistant Examiner*—Vera C. Clarke
*Attorney, Agent, or Firm*—Gunar J. Blumberg; William H. Magidson; Ralph C. Medhurst

[57] ABSTRACT

A process for producing fiber grade terephthalic acid is disclosed. In this process impurities having high molecular weight are eliminated by hydrogenation comprising the following steps: (a) treating an aqueous solution containing at least about 1 percent of said impure terephthalic acid with hydrogen at a temperature in the range of about 300° F. to about 450° F. and at a pressure sufficient to maintain the solution in the liquid phase in the presence of a supported or unsupported metallic Group VIII noble metal catalyst wherein both the metal and support components are insoluble in the solution at the temperature and at a hydrogen partial pressure of from about 30 to about 300 pounds per square inch; (b) separating the treated solution from the catalyst; (c) crystallizing terephthalic acid from the separated solution while retaining impurities and the reduced aromatic compounds dissolved in the resulting mother liquor at a temperature in the range of about 100° F. to about 450° F.; and (d) separating the mother liquor as a liquid phase containing dissolved impurities and reduction products from said crystals while continuing to maintain a temperature in the range of about 100° F. to about 450° F. whereby purified crystals of fiber grade terephthalic acid are recovered. Purified terephthalic acid is useful as a starting material in the manufacture of polyethylene terephthalate which is the principal polymer for polyester fibers, films, and resins for bottles.

14 Claims, No Drawings

PROCESS FOR REMOVAL OF HIGH MOLECULAR WEIGHT IMPURITIES IN THE MANUFACTURE OF PURIFIED TEREPHTHALIC ACID

TECHNICAL FIELD

This invention relates to a method for purification of terephthalic acid.

BACKGROUND OF THE INVENTION

Polymer grade terephthalic acid is the starting material for polyethylene terephthalate (PET), which is the principal polymer for polyester fibers, polyester films, and resins for bottles and the like containers. Polyester fibers are used in textiles as well as in industrial applications such as tire cord. Polyester films coated with adhesives and emulsions are useful as wrapping tapes, photographic films, recording tapes, and the like.

Polymer grade terephthalic acid is derived from relatively less pure, technical grade terephthalic acid by purification of the latter utilizing hydrogen and a noble metal catalyst as described in U.S. Pat. No. 3,584,039 to Mexer. In the purification process, the impure terephthalic acid is dissolved in water at an elevated temperature, and the resulting solution hydrogenated, preferably in the presence of a hydrogenation catalyst, e.g., palladium on a carbon support, as described in U.S. Pat. No. 3,726,915 to Pohlmann. This hydrogenation step converts the various color bodies present in the relatively impure terephthalic acid to colorless products. The principal feedstock impurity, 4-carboxybenzaldehyde, is converted to p-toluic acid.

The resulting purified product, polymer grade terephthalic acid, is recovered by crystallization, centrifugation, and drying. Another related purification-by-hydrogenation process for aromatic polycarboxylic acids produced by liquid-phase catalytic oxidation of polyalkyl aromatic hydrocarbons is described in U.S. Pat. No. 4,405,809 to Stech et al. Purification of terephthalic acid by modulating hydrogen concentration is disclosed in my U.S. Pat. No. 4,626,598 granted on Dec. 2, 1986 and incorporated herein by reference.

However, the variable nature of the impure terephthalic acid feedstock makes process control, and thus quality assurance, difficult and costly. To this end, it would be desirable to effect hydrogenation of an aqueous, impure terephthalic acid solution under conditions that optimize the reduction of specific colored compounds identified as causing the yellow color of improperly purified terephthalic acid. The present invention provides a convenient method for reducing specific colored aromatic compounds which cause the color problems in terephthalic acid.

SUMMARY OF THE INVENTION

It has now been found that the color of terephthalic acid purified by hydrogenation is inversely proportional to the solution hydrogen concentration in a relatively impure, aqueous terephthalic acid solution which is hydrogenated and from which the purified terephthalic acid has been derived. Thus, the color level of purified terephthalic acid in batch or continuous processes can be controlled effectively so as to reduce the concentration of high molecular weight aromatic compounds in terephthalic acid. An increase in the solution hydrogen concentration results in a decrease in the color level of the purified terephthalic acid, and vice versa. The modulation is effected in direct or indirect response to the b*-value of the produced terephthalic acid on the Hunter Color Scale by adjusting reactor hydrogen partial pressure and/or hydrogen flow rate into the impure aqueous solution.

In a continuous purification process, solution hydrogen concentration in the hydrogenation reactor can be adjusted directly on the basis of b*-value change in the obtained purified product or indirectly on the basis of a change in optical density of the feed solution to a light beam having a wavelength of 340 nanometers (nm), the b*-value change being a function of the optical density change at 340 nm for given hydrogenation conditions.

Specifically, it has been found that a 0.1-unit change in the b*-value of the obtained product, i.e., terephthalic acid, can be compensated by an adjustment of dissolved hydrogen concentration in the impure terephthalic acid solution in the range of about 0.03 to about 0.3 cubic centimeters/gram (cc/g), depending upon the activity of the particular catalyst that is employed. The volume of dissolved hydrogen is that at 1 atmosphere absolute pressure and 0° C. (32° F.).

Thus, a 0.1-unit change in the b*-value of the obtained product can also be compensated, depending upon the activity of the catalyst employed, by an adjustment in reactor hydrogen partial pressure of as little as about 5 pounds per square inch (psi) to as high as about 60 psi. An increase in reactor hydrogen partial pressure results in a decrease in the product b*-value, and a decrease in reactor hydrogen partial pressure results in an increase in the product b*-value. Also, a 0.1-unit change in feed optical density to light having a wavelength of 340 nanometers (nm) can cause about a 0.05-unit change in the b*-value of the purified terephthalic acid obtained from that feed. Accordingly, a 0.1-unit change in the feed optical density at 340 nm can be compensated as well by an adjustment in reactor hydrogen partial pressure of as little as about 2.5 psi to as high as about 30 psi.

I have discovered a process for producing fiber grade terephthalic acid from an impure terephthalic acid having as impurities high molecular weight aromatic compounds derived from catalytic liquid-phase oxidation of paraxylene with molecular oxygen, wherein the improved process comprises the following sequence of operations: (a) treating an aqueous solution containing at least about 5 percent of said impure terephthalic acid with hydrogen at a temperature in the range of about 450° F. to about 600° F. and at a pressure sufficient to maintain the solution in the liquid phase in the presence of a supported or unsupported metallic Group VIII Noble metal catalyst wherein both the metal and support components are insoluble in the solution at the temperature and at a hydrogen partial pressure of from about 10 to about 200 pounds per square inch; (b) separating the treated solution from the catalyst; (c) crystallizing terephthalic acid from the separated solution while retaining impurities and the reduced aromatic compounds dissolved in the resulting mother liquor at a temperature in the range of about 300° F. to about 450° F.; and (d) separating the mother liquor as a liquid phase containing dissolved impurities and reduction products from said crystals while continuing to maintain a temperature in the range of about 300° F. to about 450° F. whereby purified crystals of fiber-grade terephthalic acid are recovered.

In a process for producing fiber grade terephthalic acid from an impure terephthalic acid having as impurities high molecular weight aromatic compounds derived from catalytic liquid-phase oxidation of paraxylene with molecular oxygen, wherein the improved process comprises the following sequence of operations: (a) treating an aqueous solution containing at least about 0.1 percent of said impure terephthalic acid having as its major impurities 3,7-Dicarboxybenz[c]coumarin hereinafter (3,7-DCBc), 2,4',5-Tricarboxybiphenyl hereinafter (TCBi), 2,6-Dicarboxyfluorenone hereinafter (DCF), 2,5-Dicarboxyphenyl-4-Carboxyphenylmethane hereinafter (CDM), Bis(4-carboxyphenyl)methane hereinafter (BCPM), 3,4'-Dicarboxybiphenyl hereinafter (3,4'-DCBi), 4,4'-Dicarboxybiphenyl hereinafter (4,4'-DCBi), and 2,6-Dicarboxyfluorene hereinafter (DCFe) with hydrogen at a temperature in the range of about 300° F. to about 450° F. and at a pressure sufficient to maintain the solution in the liquid phase in the presence of a supported or unsupported metallic Group VIII noble metal catalyst wherein both the metal and support components are insoluble in the solution at the temperature and at a hydrogen partial pressure of from about 30 to about 300 pounds per square inch; (b) separating the treated solution from the catalyst; (c) crystallizing terephthalic acid from the separated solution while retaining impurities and the reduced aromatic compounds dissolved in the resulting mother liquor at a temperature in the range of about 300° F. to about 450° F.; and (d) separating the mother liquor as a liquid phase containing dissolved impurities and reduction products from said crystals while continuing to maintain a temperature in the range of about 200° F. to about 350° F. whereby purified crystals of fiber grade terephthalic acid are recovered.

In my process the catalytic hydrogen treatment is effected at a temperature of about 250° F. to about 450° F. In my process the concentration of terephthalic acid in the aqueous solution is in the range of about 0.1 to about 10 percent.

This process is particularly applicable to treating an aqueous solution containing at least about 1% of said impure terephthalic acid having as its major impurities: 3,7-DCBc, TCBi, DCF, CDM, BCPM, 3,4'-DCBi, 4,4'-DCBi, and DCFe. Preferably the catalytic hydrogen treatment is affected at a temperature of about 300° F. to about 400° F. wherein the concentration of terephthalic acid in the aqueous solution is in the range of about 0.5% to about 2% and wherein the catalyst is palladium extended on a carbon support. Alternatively, it is suitable to conduct my novel process wherein the aqueous solution and hydrogen are percolated through a particular metallic palladium extending on a carbon support. The hydrogen is usually at a partial pressure of about 100 to about 200 pounds per square inch and is introduced continuously with an aqueous solution. Suitably, in my process, the hydrogenated impurities are returned to the oxidation reactor.

The purified terephthalic acid is useful for direct esterification with a diol, e.g., ethylene glycol, followed by polycondensation to produce relatively high molecular weight polyesters that can be fabricated into fibers, films, sheets, and the like.

DESCRIPTION OF PREFERRED EMBODIMENTS

The process embodying the present invention is conducted at an elevated temperature and pressure with the terephthalic acid to be purified dissolved in water or like polar solvent. Water is the preferred solvent; however, other suitable polar solvents are the relatively lower molecular weight alkyl carboxylic acids, alone or admixed with water.

Reactor, and thus solution, temperatures during purification can be in the range of about 500° F. to about 600° F., preferably about 530° F. to about 550° F., and more preferably about 535° F. to about 545° F.

Reactor pressure conditions primarily depend upon the temperature at which the purification process is carried out. Inasmuch as the temperatures at which practical amounts of the impure terephthalic acid may be dissolved are substantially above the normal boiling point of the polar solvent, the process pressures are necessarily considerably above atmospheric pressure. The reactor pressure can be maintained by gaseous hydrogen alone or in admixture with an inert gas such as water vapor and/or nitrogen. The use of an inert gas in admixture with hydrogen also can provide an advantageous means for modulating the reactor hydrogen partial pressure, especially at relatively low hydrogen partial pressures. To this end, the inert gas is preferably admixed with hydrogen prior to introduction into the reactor. In general, under normal operation, the reactor pressure during hydrogenation can be in the range of about 950 to about 1,200 pounds per square inch gauge (psig).

The hydrogenation reactor can be operated in several modes. For example, a predetermined liquid level can be maintained in the reactor and hydrogen can be fed in, for any given reactor pressure, at a rate sufficient to maintain the predetermined liquid level. The difference between the actual reactor pressure and the vapor pressure of the terephthalic acid solution present is the hydrogen partial pressure in the reactor vapor space. Alternatively, if hydrogen is fed in admixture with an inert gas such as nitrogen, the difference between the actual reactor pressure and the vapor pressure of the terephthalic acid solution present is the combined partial pressure of hydrogen and the inert gas admixed therewith. In this case the hydrogen partial pressure can be calculated from the known relative amounts of hydrogen and inert gas present in the admixture.

In yet another operating mode the reactor can be filled with the terephthalic acid solution so as to provide no reactor vapor space. That is, the reactor can be operated as a hydraulically full system with hydrogen being fed to the reactor by flow control. In such an instance, the solution hydrogen concentration can be modulated by adjusting the hydrogen flow rate to the reactor. If desired, a pseudo-hydrogen partial pressure value can be calculated from the solution hydrogen concentration which, in turn, can be correlated with the hydrogen flow rate to the reactor.

In the operating mode where process control is effected by adjusting the hydrogen partial pressure, the hydrogen partial pressure in the reactor preferably is in the range of about 10 psi to about 200 psi, or higher, depending upon the service pressure rating of the reactor, the degree of contamination of the impure terephthalic acid, the activity and age of the particular catalyst employed, and like processing considerations.

In the operating mode where process control is effected by adjusting directly the hydrogen concentration in the feed solution, the latter is less than saturated with respect to hydrogen and the reactor itself is hydraulically full. Thus an adjustment of the hydrogen flow rate to the reactor will result in the desired proportional modulation of hydrogen concentration in the solution.

The amount of hydrogen supplied under reaction conditions usually is in the range of about 1 to about 5 moles in excess over the stoichiometric amount required to reduce the principal reducible impurity, 4-carboxybenzaldehyde, as well as the characteristically yellow-colored impurities that may be present.

Hydrogenation of the impure terephthalic acid solution is effected in the presence of a noble metal catalyst which can be used supported or unsupported. A wide variety of hydrogenation catalysts is available for this purpose. A typical noble metal-bearing catalyst comprises about 0.01 to about 1 weight percent of a nobel metal, calculated as the elemental metal and based on the total weight of the catalyst, supported on a porous inert support structure such as charcoal. The support structure preferably has a surface area in the range of about 1,000 to about 2,000 square meters per gram. Nobel metals particularly well-suited as catalysts for the present purposes are platinum and palladium. A particularly preferred catalyst is palladium on carbon.

Other catalysts effective for aqueous phase hydrogenation under the relatively mild hydrogenation conditions described hereinabove are listed in Kirk-Othmer, *Encyclopedia of Chemical Technology* (Wiley-Interscience), particularly in the chapters on Hydrogenation and Catalysts. See also U.S. Pat. Nos. 2,070,770 to Amend and No. 2,105,664 to Lazier. Illustrative other Group VIII noble metals suitable as catalysts for the present purposes are ruthenium, rhodium, osmium, and iridium.

The present purification process can be carried out in a batch mode as well as a continuous mode. For commercial scale purification of terephthalic acid the continuous mode is preferred. In any event, however, the color of the obtained purified terephthalic acid is monitored and the hydrogen partial pressure in the reactor adjusted so as to maintain the desired color level of the purified product.

The color level of the purified product can be monitored or evaluated directly or indirectly, as described hereinbelow. The reactor hydrogen partial pressure is then adjusted to compensate for any detected impermissible deviation from the desired color level.

The color level of the purified product can be ascertained by measuring its b*-value on the Hunter Color Scale as described in Hunter, *The Measurement of Appearance,* Chapter 8, pp. 103–132, John Wiley & Sons, N.Y., N.Y. (1975), and in Wyszecki et al., *Color Science, Concepts and Methods, Quantitative Data and Formulae,* 2d Ed., pp. 166–168, John Wiley & Sons, N.Y., N.Y. (1982).

More specifically, the b*value of purified terephthalic acid can be determined using, for example, a Diano Match Scan Spectrophotometer as follows. Purified terephthalic acid is pressed into a pellet having a thickness of about 0.25 inch and a diameter of about 1 inch. The pellet is then irradiated with white light that has been UV-filtered. The spectrum of the visible light reflected from the sample is determined and tristimulus values (X, Y, and Z) are computed using the CIE Standard Observer functions. Using the weighted-ordinate method, tristimulus values are obtained from the following equations:

$$X = \sum_{400}^{700} R_\lambda x_\lambda, \quad Y = \sum_{400}^{700} R_\lambda y_\lambda, \quad Z = \sum_{400}^{700} R_\lambda z_\lambda,$$

where $R\lambda$ is the percent reflectance of the object at wavelength $\lambda$ and $x\lambda$, $y\lambda$, and $z\lambda$ are the Standard Observer functions at wavelength $\lambda$ for CIE Illuminant D65. The tristimulus values X, Y and Z, identify the color of the object in terms of the mixture of the primary lights that match it visually. Tristimulus values, however, are of limited use as color specifications, because they do not correlate with visually meaningful attributes of color appearance and are not uniform in the spacing of colors as related to visual differences. As a result, "Uniform Color Scales" (UCS) have been adopted which use simple equations to approximate visual response. The UCS scale used by the Diano instrument is the CIE 1976 L*a*b* formula which converts tristimulus values to L*, a*, and b* values as shown below:

$$L^* = 25(100Y/Y_o)^{\frac{1}{3}} - 16$$

$$a^* = 500[(X/X_o)^{\frac{1}{3}} - (Y/Y_o)^{\frac{1}{3}}]$$

$$b^* = 200[(Y/Y_o)^{\frac{1}{3}} - (Z/Z_o)^{\frac{1}{3}}]$$

The L*-value is a measure of the luminosity or whiteness of an object where L*=100 is pure white, L*=0 is black, and in-between is gray. The L*-value is strictly a function of the tristimulus Y-value. The b*-value is a measure of the yellowness-blueness attribute where positive b*-values represent yellow appearance and negative b*-values represent blue appearance. The b*-value is a function of both tristimulus values Y and Z.

Alternatively, by the aforesaid indirect method, the color level, e.g., b*-value, of the purified product can be correlated with the optical density (OD) of the incoming impure terephthalic acid solution feed to the reactor by routine tests and the optical density of the incoming feed utilized to adjust the reactor hydrogen partial pressure. Typically, the optical density values can be determined using a spectrophotometer and a light beam having a wavelength of 340 nanometers (nm) or millimicrons (mu), correlated with the product b*-value at a given hydrogen partial pressure for a specific catalyst, and then used to adjust the hydrogen partial pressure during a particular process run so as to produce a purified product having the desired b*-value.

It has been found that a 0.1-unit deviation in the b*-value of a product can be compensated by an adjustment in reactor hydrogen partial pressure of as low as about 5 psi to as high as about 60 psi, depending upon the activity of the catalyst employed. If a fresh, relatively high activity catalyst is utilized, the initial adjustment in hydrogen partial pressure for a 0.1-unit deviation in the b*-value usually is about 5 psi to about 7.5 psi. However, as the catalyst stabilizes, the adjustment in hydrogen partial pressure for a 0.1-unit deviation in the b*-value usually is about 40 psi to about 50 psi.

Similarly, it has been found that a 0.1-unit change in feed solution optical density at 340 nm($O_{340}$) causes about a 0.05-unit change in the b*-value of the purified terephthalic acid that is derived from that particular feed solution. Thus, a 0.1-unit change in $OD_{340}$ of the feed solution usually can be initially compensated by an adjustment in reactor hydrogen partial pressure of about 2.5 psi to about 4 psi for a fresh, relatively high activity catalyst. However, as the activity of catalyst stabilizes during use, a 0.1-unit change in $OD_{340}$ of the feed solution usually can be compensated by an adjustment in reactor hydrogen partial pressure of about 20 psi to about 25 psi.

The overall relationship among b*-value, hydrogen partial pressure, and optical density at 340 nm can also be expressed as $$b^{*}\text{-value} \alpha\ A(H_2pp) + C(OD_{340})$$

wherein $H_2$ pp designates hydrogen partial pressure expressed in psi, $OD_{340}$ is the optical density value of the crude terephthalic acid feed solution, A has a value of about 0.001 to about 0.03, and C has a value of about 0.4 to about 1.4.

Similarly, the overall relationship among b*-value, solution hydrogen concentration, and optical density at 340 nm can be expressed as $$b^{*}\text{-value} \alpha\ D(H_2conc.) + C(OD_{340})$$

wherein $H_2$ conc. designates solution hydrogen concentration in cubic centimeters of hydrogen at 1 atmosphere absolute pressure and 0° C. (32° F.) dissolved per gram of crude terephthalic acid feed solution, $OD_{340}$ is the optical density value of the crude terephthalic acid feed solution, D has a value of about 0.2 to about 5.75, and C has a value of about 0.4 to about 1.4.

If it is desired to modulate the solution hydrogen concentration in a hydraulically full reactor directly by adjusting the flow of gaseous hydrogen to the hydrogenation reactor, then in such an event the hydrogen flow rate can be adjusted to provide a change in solution hydrogen concentration in the range of about 0.03 cc/g to about 0.3 cc/g for a 0.1-unit change in the product b*-value to be implemented, or in the range of about 0.015 cc/g to about 0.15 cc/g for an observed 0.1-unit change in $OD_{340}$ of the feed solution to the hydrogenation reactor.

The terephthalic acid concentration in the solution to be purified by hydrogenation can vary over a relatively wide range. The concentration can be as low as about 5 percent by weight or as high as about 35 percent by weight, based on the weight of the solution. Preferably the solution concentration of terephthalic acid is in the range of about 10 to about 30 percent by weight.

The present invention is illustrated by the following Examples.

EXAMPLE A

A sample of 1.0 g of PTA mother liquor solids was dissolved in 1,000 ml of $H_2O$ in the presence of 200 mg of palladium black at 300° F. in a titanium autoclave. After the reaction temperature had been maintained for 1 hour, a sample was taken and, after 300 psi of $H_2$ was added, additional samples were obtained. The total reactor effluent samples were analyzed by high performance liquid chromatography (HPLC) and the data is given in Table I. This Table shows that high molecular weight components known to be formed during hydrogen treatment reactions, were reduced up to 98 percent. 4,4'-DCBi was not reduced. No increase in the concentration of any other components using 254 nm absorbance detection was observed and therefore I concluded that the high molecular weight impurities were eliminated by ring hydrogenation.

TABLE I

Hydrogen Treatment of PTA ML Solids

| Component | Concentration at | | | |
|---|---|---|---|---|
| | 0 min | 15 min | 30 min | 60 min |
| 3,7-DCBc | 322 | nd | nd | nd |
| TCBi | 1516 | 85 | 40 | 11 |
| DCF | 516 | 8 | nd | nd |
| CDM | 197 | 33 | nd | nd |
| BCPM | 117 | 15 | 4 | 2 |
| 3,4'-DCBi | 2298 | 105 | 36 | 15 |
| 4,4'-DCBi | 932 | 218 | 155 | 49 |
| DCFe | 2273 | 225 | 97 | 44 |
| RFC(uv) | 1637 | 105 | nd | nd |
| RFC(vis) | 1061 | 69 | nd | nd |

EXAMPLE B

To determine the effect of catalytic hydrogen treatment on TA and p-toluic acid, the experiment was repeated and the total reactor effluent samples obtained were dissolved in dilute ammonium hydroxide. To determine the relative changes in the concentration of TA, the absorbance of the ammonium hydroxide solutions was measured at 290 nm (Table II). Note that the small changes in IA concentrations were within analytical variability. In addition, a portion of each ammonium hydroxide solution was chromatographically separated and the concentration of p-toluic acid was determined for each sample (Table: III). As with TA, the concentration of p-toluic acid remained essentially unchanged.

TABLE II

Effect of Hydrogen Treatment on TA Concentration

| Time (min.) | OD290 | TA Conc (g/100 ml)[a] | 100% Recovery[b] |
|---|---|---|---|
| 0 | 0.071 | 0.041 | 108 |
| 15 | 0.065 | 0.038 | 100 |
| 30 | 0.066 | 0.039 | 103 |
| 60 | 0.064 | 0.037 | 97 |

[a]Total reactor effluent TA concentrations are given after dissolving in 100 ml of $NH_4OH$.
[b]100% recovery is 0.038 g/100 ml since the sample bombs have a volume of 44 ml.

These data demonstrate that high molecular weight impurities in PTA mother liquor solids can be selectively reduced by ring hydrogenation while the major components, TA and p-toluic acid, are not reacted. These significant results are unexpected because ring hydrogenation of high molecular weight impurities is not observed under PTA process conditions.

The effect of hydrogen treatment in p-toluic acid is shown in Table III.

TABLE III

Effect of Hydrogen Treatment on p-Toluic Acid

| Time (min.) | p-Toluic Acid (%) |
|---|---|
| 0 | 9.00 |
| 15 | 9.21 |
| 30 | 8.85 |
| 60 | 9.28 |

EXAMPLE C

To determine the influence of catalyst life on reaction activity and selectivity, a solution of PTA mother liquor solids was hydrogen treated using a continuous experimental unit. A total of approximately 600 lb. of solution was treated using a hydrogen partial pressure of 170 psi and 2 wt.% palladium on carbon (4×8 mesh)

catalyst (30 grams) at a temperature of 400° F. Table IV provides comparison of component concentrations in the feed and the hydrogen treated products taken near the end of the experiment. The data demonstrate that selectivity has been maintained and that activity for reduction of high molecular weight components is high.

TABLE IV

| Continuous Hydrogen Treatment of PTA Mother Liquor Solids | | | |
|---|---|---|---|
| | Feed | Product | Product |
| Lbs. slurry pumped | | 462 | 562 |
| Wt. % solids | | 0.98 | 1.08 |
| % TA | 68.4 | 68.5 | 67.9 |
| % p-Toluic Acid | 18.1 | 18.0 | 17.6 |
| OD(340) (au/g) | 0.387 | 0.103 | 0.101 |
| DCFe | 10,800 | 4,134 | 3,739 |
| RFC(uv) | 15,175 | 2,095 | 2,074 |
| RFC(vis) | 11,085 | 309 | 315 |

What is claimed is:

1. In a process for producing fiber grade terephthalic acid from an impure terephthalic acid having as impurities high molecular weight aromatic compounds derived from catalytic liquid-phase oxidation of paraxylene with molecular oxygen, wherein the improved process comprises the following sequence of operations:
   (a) treating an aqueous solution containing at least about 5 percent of said impure terephthalic acid with hydrogen at a temperature in the range of about 450° F. to about 600° F. and at a pressure sufficient to maintain the solution in the liquid phase in the presence of a supported or unsupported metallic Group VIII noble metal catalyst wherein both the metal and support components are insoluble in the solution at the temperature and at a hydrogen partial pressure of from about 10 to about 200 pounds per square inch to ring hydrogenate said impurities;
   (b) separating the treated solution from the catalyst;
   (c) crystallizing terephthalic acid from the separated solution while retaining impurities and the reduced aromatic compounds dissolved in the resulting mother liquor at a temperature in the range of about 300° F. to about 450° F.;
   (d) separating the mother liquor as a liquid phase containing dissolved impurities and reduction products from said crystals while continuing to maintain a temperature in the range of about 300° F. to about 450° F. whereby purified crystals of fiber grade terephthalic acid are recovered; and
   (e) returning the mother liquor as a liquid phase containing dissolved impurities and reduction products to the oxidation reactor.

2. The process of claim 1 wherein the catalytic hydrogen treatment is effected at a temperature within the range of about 500° F. to about 550° F. in a continuous flow system.

3. The process of claim 1 wherein the concentration of terephthalic acid in the aqueous solution is in the range of about 10 to about 30%.

4. The process of claim 1 wherein the catalyst is palladium extended on a carbon support.

5. The process of claim 1 wherein the aqueous solution and hydrogen are percolated through a bed of metallic palladium extended on a carbon support.

6. The process of claim 5 wherein hydrogen at a partial pressure of about 50 to about 100 pounds per square inch is introduced continuously with an aqueous solution.

7. The process of claim 2 wherein the separation of mother liquor containing dissolved impurities from precipitated catalysts is effected at a temperature in the range of about 300° F. to about 450° F. and the mother liquor is recycled to the oxidation reactor.

8. In a process for producing fiber grade terephthalic acid from an impure terephthalic acid having as impurities high molecular weight aromatic compounds derived from catalytic liquid-phase oxidation of paraxylene with molecular oxygen, wherein the improved process comprises the following sequence of operations:
   (a) treating an aqueous solution containing at least about 0.1 percent of said impure terephthalic acid having as its major impurities 3,7-dicarboxybenz[c]coumarin, 2,4',5-tricarboxybiphenyl, 2,6-dicarboxyfluorenone, 2,5-dicarboxyphenyl-4-carboxyphenylmethane, bis(4-carboxyphenyl)methane, 3,4'-dicarboxybiphenyl, 4,4'-dicarboxybiphenyl, and 2,6-dicarboxyfluorene with hydrogen at a temperature in the range of about 300° F. to about 450° F. and at a pressure sufficient to maintain the solution in the liquid phase in the presence of a supported or unsupported metallic Group VIII noble metal catalyst wherein both the metal and support components are insoluble in the solution at the temperature and at a hydrogen partial pressure of from about 30 to about 300 pounds per square inch to ring hydrogenate said impurities;
   (b) separating the treated solution from the catalyst;
   (c) crystallizing terephthalic acid from the separated solution while retaining impurities and the reduced aromatic compounds dissolved in the resulting mother liquor at a temperature in the range of about 250° F. to about 450° F.;
   (d) separating the mother liquor as a liquid phase containing dissolved impurities and reduction products from said crystals while continuing to maintain a temperature in the range of about 100° F. to about 450° F. whereby purified crystals of fiber grade terephthalic acid are recovered; and
   (e) returning the mother liquor as a liquid phase containing dissolved impurities and reduction products to the oxidation reactor.

9. The process of claim 8 wherein the catalytic hydrogen treatment is effected at a temperature within the range of about 300° F. to about 450° F. in a continuous flow system.

10. The process of claim 8 wherein the concentration of terephthalic acid in the aqueous solution is in the range of about 0.1 to about 10%.

11. The process of claim 8 wherein the catalyst is palladium extended on a carbon support.

12. The process of claim 8 wherein the aqueous solution and hydrogen are percolated through a bed of metallic palladium extended on a carbon support.

13. The process of claim 12 wherein hydrogen at a partial pressure of about 30 to about 300 pounds per square inch is introduced continuously with an aqueous solution.

14. The process of claim 9 wherein the separation of mother liquor containing dissolved impurities from precipitated catalysts is effected at a temperature in the range of about 200° F. to about 300° F. and the mother liquor is recycled to the oxidation reactor.

* * * * *

UNITED STATES PATENT AND TRADEMARK OFFICE
CERTIFICATE OF CORRECTION

PATENT NO. : 4,782,181

DATED : November 1, 1988

INVENTOR(S) : David E. James

It is certified that error appears in the above-identified patent and that said Letters Patent is hereby corrected as shown below:

Column | Line(s)
--- | ---
5 | 56 | "'b*value" should read --b*-value--
6 | 1-4 | "$X = \sum_{400}^{700} R\lambda x\lambda, Y = \sum_{400}^{700} R\lambda y\lambda, Z = \sum_{400}^{700} R\lambda z\lambda,$" should read --$X = \sum_{400}^{700} R\lambda \bar{x}\lambda, Y = \sum_{400}^{700} R\lambda \bar{y}\lambda, Z = \sum_{400}^{700} R\lambda \bar{z}\lambda,$--
6 | 63 | "($O_{340}$)" should read --($OD_{340}$)--
8 | 25 | "IA" should read --TA--
8 | 29 | "(Table: III)." should read --(Table III).--

Signed and Sealed this

Eleventh Day of July, 1989

Attest:

DONALD J. QUIGG

Attesting Officer

Commissioner of Patents and Trademarks